United States Patent
Xi et al.

(10) Patent No.: US 9,089,276 B2
(45) Date of Patent: Jul. 28, 2015

(54) SYSTEMS AND METHODS FOR OBTAINING SUBSTANTIALLY SIMULTANEOUS MULT-CHANNEL IMPEDANCE MEASUREMENTS AND RELATED APPLICATIONS

(71) Applicant: Pacesetter, Inc., Sunnyvale, CA (US)

(72) Inventors: Cecilia Qin Xi, San Jose, CA (US); Jimmy Johansson, Solna (SE); Allan Olson, Spanga (SE); Weiqun Yang, Cupertino, CA (US)

(73) Assignee: Pacesetter, Inc., Sunnyvale, CA (US)

( * ) Notice: Subject to any disclaimer, the term of this patent is extended or adjusted under 35 U.S.C. 154(b) by 0 days.

(21) Appl. No.: 13/838,581

(22) Filed: Mar. 15, 2013

(65) Prior Publication Data

US 2014/0276151 A1 Sep. 18, 2014

(51) Int. Cl.
| | |
|---|---|
| *A61B 5/04* | (2006.01) |
| *A61B 5/053* | (2006.01) |
| *A61B 5/029* | (2006.01) |
| *A61N 1/362* | (2006.01) |
| *A61N 1/368* | (2006.01) |
| *A61N 1/365* | (2006.01) |
| *G06F 19/00* | (2011.01) |

(52) U.S. Cl.
CPC ............. *A61B 5/0538* (2013.01); *A61B 5/029* (2013.01); *A61B 5/04* (2013.01); *A61N 1/368* (2013.01); *A61N 1/3622* (2013.01); *A61N 1/36521* (2013.01); *G06F 19/3406* (2013.01)

(58) Field of Classification Search
CPC ...... A61B 5/0538; A61B 5/045; A61B 5/029; A61N 1/3622; A61N 1/368; A61N 1/36521; G06F 19/3406

USPC .............. 600/508, 509; 607/4, 9, 17, 27, 116
See application file for complete search history.

(56) References Cited

U.S. PATENT DOCUMENTS

| | | | |
|---|---|---|---|
| 5,501,702 A | 3/1996 | Plicchi | |
| 6,278,894 B1 | 8/2001 | Salo | |
| 6,684,101 B2 | 1/2004 | Daum | |
| 6,754,530 B2 | 6/2004 | Bakels | |
| 7,149,573 B2 | 12/2006 | Wang | |
| 7,313,434 B2 | 12/2007 | Belalcazar | |
| 7,711,423 B2 | 5/2010 | Burnes | |
| 7,925,349 B1 * | 4/2011 | Wong et al. | 607/28 |
| 8,010,196 B1 | 8/2011 | Wong | |
| 2006/0173364 A1 * | 8/2006 | Clancy et al. | 600/485 |
| 2009/0088812 A1 * | 4/2009 | Wulfman | 607/9 |
| 2010/0030289 A1 * | 2/2010 | Casavant et al. | 607/4 |
| 2012/0035495 A1 | 2/2012 | Gutfinger | |

* cited by examiner

*Primary Examiner* — Eric D. Bertram
*Assistant Examiner* — Pamela M Bays
(74) *Attorney, Agent, or Firm* — Theresa A. Raymer

(57) ABSTRACT

An implantable system includes terminals, a pulse generator, a sensing circuit, separate signal processing channels, and first, second and third multiplexers. The terminals are connected to electrodes via conductors of leads. Different subsets of the electrodes are used to define different electrical pulse delivery vectors, and different subsets of the electrodes are used to define different sensing vectors. The pulse generator produces electrical pulses, and the sensing circuit senses a signal indicative of an impedance associated with a selected sensing vector. The first multiplexer selectively connects outputs of the pulse generator to a selected one of the different electrical pulse delivery vectors at a time. The second multiplexer selectively connect inputs of the sensing circuit to a selected one of the different sensing vectors at a time. The third multiplexer selectively connects an output of the sensing circuit to one of the plurality of separate signal processing channels at a time.

14 Claims, 7 Drawing Sheets

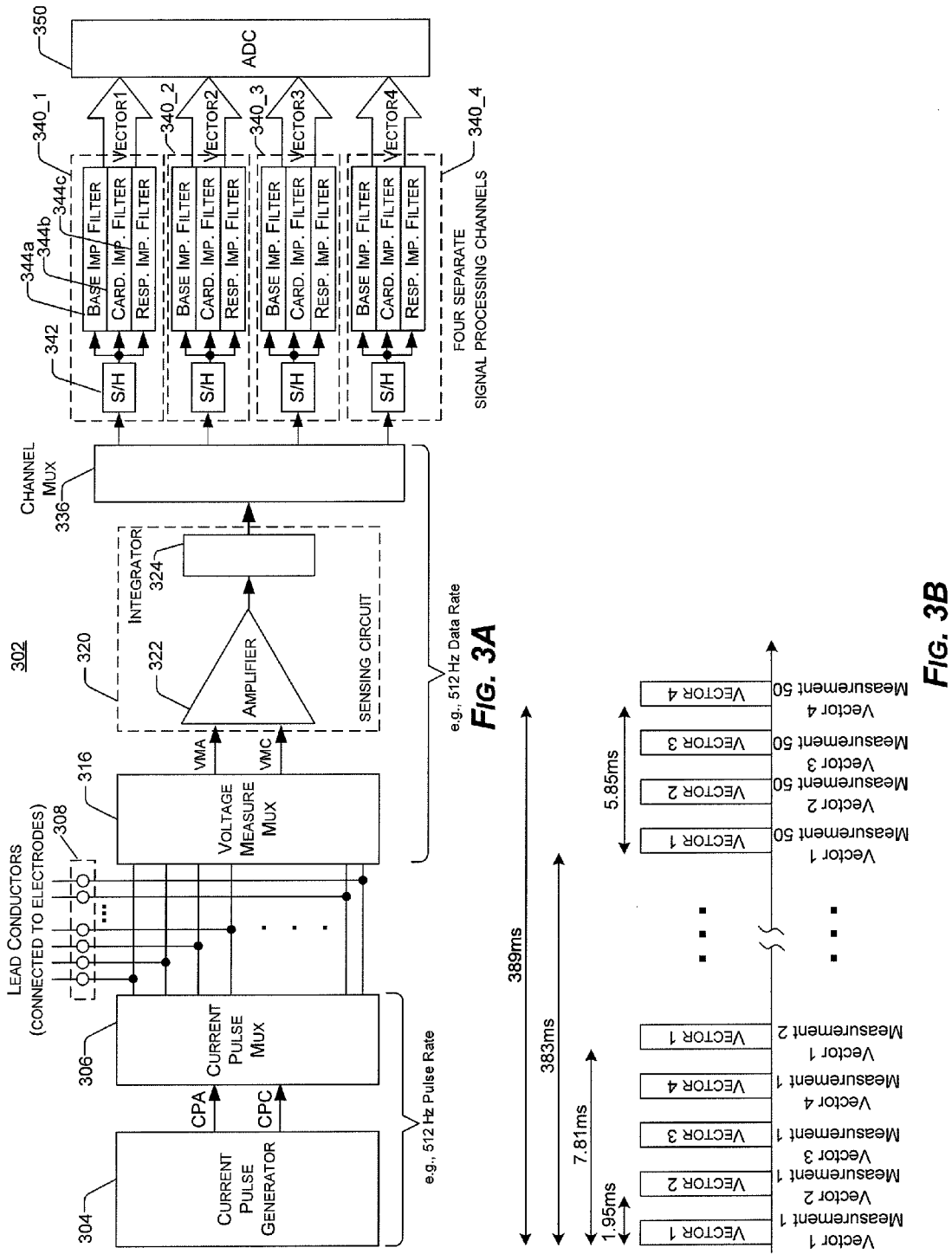

SYSTEMS AND METHODS FOR OBTAINING SUBSTANTIALLY SIMULTANEOUS MULT-CHANNEL IMPEDANCE MEASUREMENTS AND RELATED APPLICATIONS

TECHNICAL FIELD

Subject matter presented herein relates generally to implantable medical devices and related systems and methods that are capable of obtaining impedance measurements and monitoring cardiac and other conditions based on such measurements.

BACKGROUND

Implantable medical devices have been used to obtain various types of dynamic and non-dynamic impedance measurements. Examples of dynamic impedance measurements include low frequency impedance Zo (sometimes also referred to as raw impedance, or low frequency raw impedance), respiratory impedance Zr, and cardiogenic impedance Zc (sometime also referred to as cardiac impedance). A lead impedance measurement is an example of a non-dynamic impedance measurement. These various types of impedance measurements have been used for many different types of applications. For example, cardiogenic impedance signals have been used for monitoring hemodynamic stability, performing arrhythmia discrimination, prediction and monitoring of heart failure progression, and functioning as a hemodynamic (such as stroke volume) surrogate. For another example, respiratory impedance signals have been used to monitor respiratory rate and respiratory volume. However, impedance signals typically have various limitations. For example, the amplitude of an impedance signal is typically relatively small, the signal is typically susceptible to noise, and the signal typically is susceptible to changes in activity and body posture. Particularly, while a single impedance vector may have a good signal-to-noise ratio, it may have a small signal amplitude variation, or poor morphology consistency across different subjects (i.e., patients). In addition, the good and bad aspects of a vector may not be consistent across different subjects. For example, a vector with good signal variation in one patient may not yield good signal variation in another patient. Therefore, it is difficult to select a single impedance vector that will have consistent characteristics for various patients and applications.

FIG. 1 includes an upper plot of an exemplary cardiogenic impedance signal, and a lower plot of a corresponding intracardiac electrogram (IEGM) signal. Referring to the upper plot, the exemplary cardiogenic impedance signal has an overall consistency across patients, but is noisy and has very small variations for some patients. In addition, in order to obtain a representative morphology and reduce overall noise, an adequate number of beats may need to be collected, for example, 50-100 beats, which may require up to 2 minutes. Continuing with this example, if measurements from four different vectors are being made, up to 8 minutes may be required (i.e., up to 2 minutes per vector, for each of four vectors). As compared to other diagnostics features or data collection techniques, this is extremely time consuming. Therefore, a method to collect several impedance vector signals substantially simultaneously would be very beneficial.

FIGS. 2A and 2B will now be used to illustrate how prior art impedance measurement and processing circuitry 202 can be used to measure one impedance vector at a time using an exemplary maximum sampling rate of 128 Hz. More specifically, FIG. 2A is a high level block diagram illustrating the impedance measurement and processing circuitry 202, and FIG. 2B is a corresponding timing diagram that is used to explain the operation and limitations associated with the circuitry 202 shown in FIG. 2A.

Referring to FIG. 2A, the prior art impedance measurement and processing circuitry 202 includes of a current pulse generator 204 and a current pulse multiplexer 206, which can also be referred to as an output multiplexer. The multiplexer 206 connects to all of the electrodes (patient nodes) in the system such that impedance can be measured for any electrode combination. More specifically, the output of the multiplexer 206 is connected to electrode terminals 208, which are electrically connected to implantable electrodes by lead conductors. The impedance measurement and processing circuitry 202 also includes a voltage measurement multiplexer 216, which can also be referred to as an input multiplexer. Additionally, the impedance measurement hardware includes a sensing circuit 220, a signal processing channel 240, and an analog-to-digital converter (ADC) 250. The sensing circuit 220 is shown as including an amplifier 222 and an integrator 224. The signal processing channel 240 is shown as including a sample-and-hold (S/H) circuit 242 and three parallel switched-capacitor filters 244a, 244b and 244c (base impedance, cardiogenic impedance and respiratory impedance filters). Using the impedance measurement and processing circuitry 202, an impedance measurement can be obtained, e.g., by sending out a current pulse between any two (or more) electrodes in the system while measuring the resulting voltage area between any two (or more) electrodes. Since the current area is known, an impedance measurement can be obtained by dividing the voltage area by the current area.

Since the impedance measurement and processing circuitry 202 only supports measurement of one vector at a time, multi-vector (or multi-channel) measurements need to be sequential. When switching to a new vector (which is done by controlling the output and input multiplexers 206 and 216) the sudden change from one impedance vector signal to another will cause an impulse response for up to several seconds in the filters 244. So, in addition to the time consuming sequential vector measurements, there is also a delay when switching between different vector measurements. This can be appreciated from the discussion of FIG. 2B below.

Referring to FIG. 2B, assuming a pulse rate and sampling rate of 128 Hz (which corresponds to one pulse generated, and one sample obtained, each 7.81 ms), and assuming that there is a desire to obtain fifty (50) impedance measurements for each of four (4) different vectors, then it takes a total of 383 ms to obtain 50 impedance measurements for the first vector (Vector 1), a total of 383 ms to obtain 50 impedance measurements for the second vector (Vector 2), a total of 383 ms to obtain 50 impedance measurements for the third vector (Vector 3), and a total of 383 ms to obtain 50 impedance measurements for the fourth vector (Vector 4). If the filters 244a, 244b, 244c of the signal processing channel 240 had an instantaneous impulse response, then the circuitry 202 can switch between Vector 1 and Vector 2 in 7.8 ms, between Vector 2 and Vector 3 in 7.8 ms, and between Vector 3 and Vector 4 in 7.8 ms, enabling 50 impedance measurements for each of the four Vectors to be obtained in 1.56 seconds, i.e., (383 ms×4)+(7.8 ms×3)=1.56 seconds. However, in actuality, since switching from one vector to another causes an impulse response for up to several seconds in the filters 244, after switching from one vector to the another vector there is a need to wait a relatively long time (e.g., at least 2 seconds, i.e., at least 2000 ms) after switching from one vector to another vector before beginning to obtain impedance measurements for the temporally later vector. Accordingly, it would actually take at least 6.56 seconds to obtain 50 impedance measurement for each of the four Vectors, i.e., (383 ms×4)+(7.8 ms×3)+(3×2 seconds)=6.56 seconds. For certain types of applications, this would be acceptable, e.g., if the measurements were being used to monitor the integrity of leads and/or electrodes. However, for other types of applications, some of which are discussed below, that total amount of time necessary to obtain the desired impedance measurements would be much too long.

SUMMARY

Specific embodiments of the present invention can be used to measure multiple impedance vectors substantially simultaneously. More specifically, an implantable system, according to an embodiment of the present invention, includes a plurality of terminals, a pulse generator, a sensing circuit, a plurality of separate signal processing channels, and first, second and third multiplexers. The plurality of terminals are configured to be connected to a plurality of implantable electrodes via electrical conductors of one or more implantable leads, wherein a plurality of different subsets of the implantable electrodes are used to define a plurality of different electrical pulse delivery vectors, and wherein a plurality of different subsets of the implantable electrodes are used to define a plurality of different sensing vectors. The pulse generator is configured to produce electrical pulses for delivery via a selected one of the plurality of different electrical pulse delivery vectors at a time. The sensing circuit is configured to sense a signal indicative of an impedance associated with a selected one of the plurality of different sensing vectors at a time. Each of the plurality of separate signal processing channels is configured to perform signal processing on a sensed signal indicative of an impedance obtained using the sensing circuit. The first multiplexer is configured to selectively connect outputs of the pulse generator to a selected one of the plurality of different electrical pulse delivery vectors at a time. The second multiplexer is configured to selectively connect inputs of the sensing circuit to a selected one of the plurality of different sensing vectors at a time. The third multiplexer is configured to selectively connect an output of the sensing circuit to one of the plurality of separate signal processing channels at a time. In specific embodiments, the first, second and third multiplexers have synchronized switching rates.

In accordance with specific embodiments, the third multiplexer and the separate impedance processing channels enable impedances associated with the separate sensing vectors to be processed in a rapid time interleaved manner such that impedances associated with the separate sensing vectors can be considered to correspond to a substantially same temporal data point.

In accordance with an embodiment, the sensing circuit includes a differential amplifier and an integrator. The differential amplifier includes a first input terminal that receives an anodal voltage from the second multiplexer, a second input terminal that receives a cathodal voltage from the second multiplexer, and an output terminal that outputs a voltage indicative of a difference between the anodal and cathodal voltages received at the first and second input terminals. The integrator integrates the voltage output by the differential amplifier to thereby produce the sensed signal that is provided to the third multiplexer.

In accordance with an embodiment, each of the plurality of separate signal processing channels includes a sample-and-hold circuit, which receives a signal from third multiplexer, and one or more switched-capacitor filters downstream of the sample-and-hold circuit. The one or more filters, of each of the separate signal processing channels, can include one or more of the following: a filter that outputs a filtered signal indicative of low frequency impedance; a filter that outputs a filtered signal indicative of cardiac impedance; and a filter that outputs a filtered signal indicative of respiratory impedance. Alternative and/or additional filters may be used.

In accordance with certain embodiments, the pulse generator, sensing circuitry, signal processing channels and the first, second and third multiplexers are used to obtain a first impedance signal using one or more sensing vector(s) spanning both a first region and a second region within a patient's thoracic cavity; and a second impedance signal using one or more further sensing vector(s) spanning the first region but not the second region. Additionally, the system also includes a processor and/or circuitry configured to subtract the second impedance signal from the first impedance signal to obtain a third impedance signal primarily corresponding to the second region. For example, the first region can include at least one atrial chamber and at least one ventricular chamber, and the second region include the at least one atrial chamber (but not the at least one ventricular chamber). This way, the third impedance signal would, obtained through the subtraction, would be primarily indicative of the at least one ventricular chamber. For another example, the first impedance signal can be indicative of both far-field impedance and near-field impedance, and the second impedance signal can be primarily indicative of the near-field impedance but not the far-field impedance. Here, third impedance signal, obtained by subtracting the second impedance signal from the first impedance signal, would be primarily indicative of the far-field impedance. Embodiments of the present invention are also directed to combining two or more impedance signals in other manners, including using weighted or non-weighted averaging to produce a combined impedance signal. Embodiments of the present invention are also directed to related methods.

This summary is not intended to be a complete description of the invention. Other features and advantages of the invention will appear from the following description in which the preferred embodiments have been set forth in detail, in conjunction with the accompanying drawings and claims.

BRIEF DESCRIPTION OF THE DRAWINGS

FIG. 3A is a block diagram of impedance measurement and processing circuitry according to an embodiment of the present invention.

FIG. 3B is a timing diagram that is used to explain the operation and benefits associated with the impedance measurement and processing circuitry shown in FIG. 3A.

DETAILED DESCRIPTION

Figure 1:
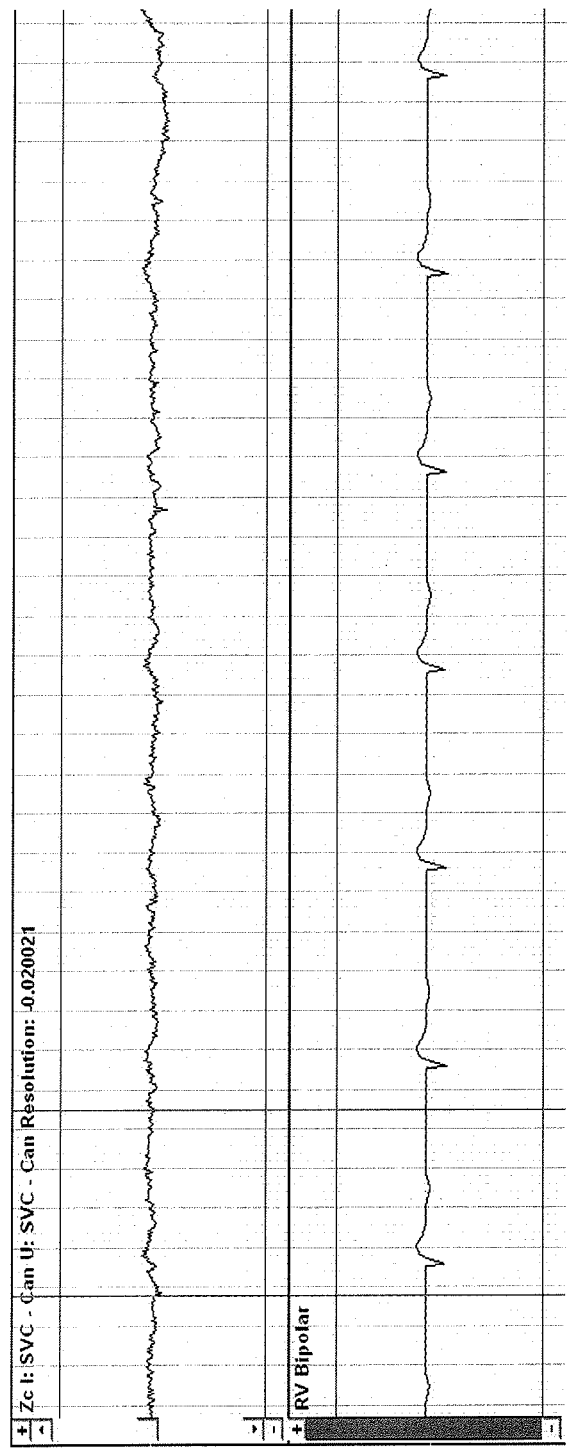
FIG. 1 includes an upper plot of an exemplary cardiogenic impedance signal, and a lower plot of a corresponding intra-cardiac electrogram (IEGM) signal.

The following description is of the best modes presently contemplated for practicing various embodiments of the present invention. The description is not to be taken in a limiting sense but is made merely for the purpose of describing the general principles of the invention. The scope of the invention should be ascertained with reference to the claims. In the description of the invention that follows, like numerals or reference designators will be used to refer to like parts or elements throughout. In addition, the first digit of a reference number identifies the drawing in which the reference number first appears.

FIGS. 3A and 3B will now be used to illustrate impedance measurement and processing circuitry 302, according to an embodiment of the present invention, that can be used to measure multiple impedance vectors in a substantially simultaneous manner. More specifically, FIG. 3A is a high level block diagram illustrating the impedance measurement and processing circuitry 302, and FIG. 3B is a corresponding timing diagram that is used to explain the operation and benefits associated with the impedance measurement and processing circuitry 302 shown in FIG. 3A.

The impedance measurement and processing circuitry 302 includes of a current pulse generator 304 and a current pulse multiplexer 306, which can also be referred to as an output multiplexer 306. The multiplexer 306 connects to all electrodes (patient nodes) in the system such that impedance can be measured for any electrode combination. More specifically, the output of the multiplexer 306 is connected to electrode terminals 308, which are electrically connected to implantable electrodes by lead conductors. The impedance measurement and processing circuitry 302 also includes a voltage measurement multiplexer 316, which can also be referred to as an input multiplexer 316. Additionally, the impedance measurement and processing circuitry 302 includes a sensing circuit 320, which is shown as including an amplifier 322 and an integrator 324, but can include additional or alternative circuitry that can be used to measure a voltage between electrodes selected by the input multiplexer 316. Up to this point, the impedance measurement and processing circuitry 302 is similar to the circuitry 202 discussed above with reference to FIG. 2A, with the exception that it will be assumed that the switching rates of multiplexers 306 and 316 are four times as fast as the switching rates of the multiplexers 206 and 216 in FIG. 2A. For example, assume that the multiplexers 306 and 316 switch at a rate of 512 Hz, whereas the multiplexers 206 and 216 have a switching rate of 128 Hz.

Still referring to FIG. 3B, the impedance measurement and processing circuitry 302 also includes a channel multiplexer 336, and multiple independent signal processing channels 340_1, 340_2, 340_3 and 340_4, which can be referred to individually as a signal processing channel 340, and can be referred to collectively of signal processing channels 340. In accordance with an embodiment, each of the signal processing channels 340 includes a sample-and-hold (S/H) circuit 342, and one or more filters 344. In FIG. 3B, each of the signal processing channels 340 is shown as including three parallel filters 344a, 344b and 344c (base impedance, cardiogenic impedance and respiratory impedance filters). In accordance with specific embodiments, the filters are implemented in a switched-capacitor configuration. However, it is noted that each of the processing channels can include more or less than three filters, and can alternatively or additionally include other types of filters. The base impedance filter 344a can be, for example, be a low pass filter having a cut-off frequency of about 2.5 Hz, which is used to output a filtered voltage signal indicative of low frequency impedance $Z_o$. The cardiac impedance filter 344b can be, for example, a bandpass filter having a bandpass frequency range of about 0.55-64 Hz, which is used to output a filtered voltage signal indicative of cardiogenic impedance $Z_c$. The respiratory impedance filter 344c can be, for example, a bandpass filter having a bandpass frequency range of about 0.06-0.70 Hz, which is used to output a filtered voltage signal indicative of respiratory impedance $Z_r$. As is well known in the art, a bandpass filter can be implemented using a low pass filter and a high pass filter. Further, it is noted that alternative cutoff frequencies and/or bandpass frequencies can be used. It is also noted that there can be more or less than four independent signal processing channels 340. However, for much of the following description, it will be assumed that the configuration shown in FIG. 3A is being implemented. The impedance measurement and processing circuitry 302 is also shown as including an analog-to-digital converter (ADC) 350 that converts analog voltage measurements/signals indicative of impedance to corresponding digital measurements/signals.

The impedance measurement and processing circuitry 302 includes the additional multiplexer 336 and the additional signal processing channels 340, as compared to the impedance measurement and processing circuitry 202 described with reference to FIG. 2A. With a higher total pulse rate, the impedance vector measurements are performed in an interleaved manner by switching measurement nodes with the output and input multiplexers 306 and 316 and directing the voltage measurements indicative of impedance to the corresponding signal processing channel 340 with the channel multiplexer 336. If for example a pulse rate of 512 Hz is used, then four (4) separate impedance vectors can be measured at 128 Hz (which is the same sampling rate described as being used with the circuitry 202 in FIGS. 2A and 2B). The small delay in switching between different nodes is negligible from the perspective of clinical analysis. The sampling rate in each of the multiple channels can vary depending on an application. For example, sampling can be programmed to 128 Hz, 64 Hz, 32 Hz and 16 Hz for channels 1 through 4, respectively. More generally, the electrical pulses for each of the vectors can be independently configured to have a different programmable pulse rate, pulse width and/or pulse amplitude than the electrical pulses for the other vectors. In addition, the multiplexer 336 can operate in a continuous mode or in a triggered mode. The trigger source can be, e.g., a command from a microprocessor (e.g., 521 in FIG. 5) or a sensed or paced event of a cardiac cycle. This feature allows for selected impedance data to be sampled and processed to reduce the current drain.

Referring now to FIG. 3B, assuming a pulse rate and sampling rate of 128 Hz for each of the four (4) different impedance vectors (which corresponds to one pulse and one sample each 7.8 ms per each of the four vectors), this corresponds to a total pulse rate and sampling rate of 512 Hz (i.e., 128 Hz×4=512 Hz). Assuming that there is a desired to obtain fifty (50) impedance measurement for each of four (4) different vectors, then it takes a total of only 389 ms to obtain 50 impedance measurements for all four vectors (which can be referred to as Vector 1, Vector 2, Vector 3 and Vector 4). More specifically, a pulse can be produced every 1.95 ms (using a pulse rate of 512 Hz), with one out of every four pulses corresponding to a different one of the four vectors. Similarly, a sample can be sensed using the sensing circuit 320 every 1.95 ms (using a sampling rate of 512 Hz), with one out of every four samples corresponding to a different one of the four vectors. In this embodiment, since each signal processing channel 340 has its own S/H 342 and its own filter(s) 344, then the impulse response associated with one vector will not affect any other vector. In other words, with this embodiment, there is not need to wait for an impulse response associated with one vector to settle before switching to another vector, since each vector has its own dedicated signal processing channel 340.

Figure 2A:
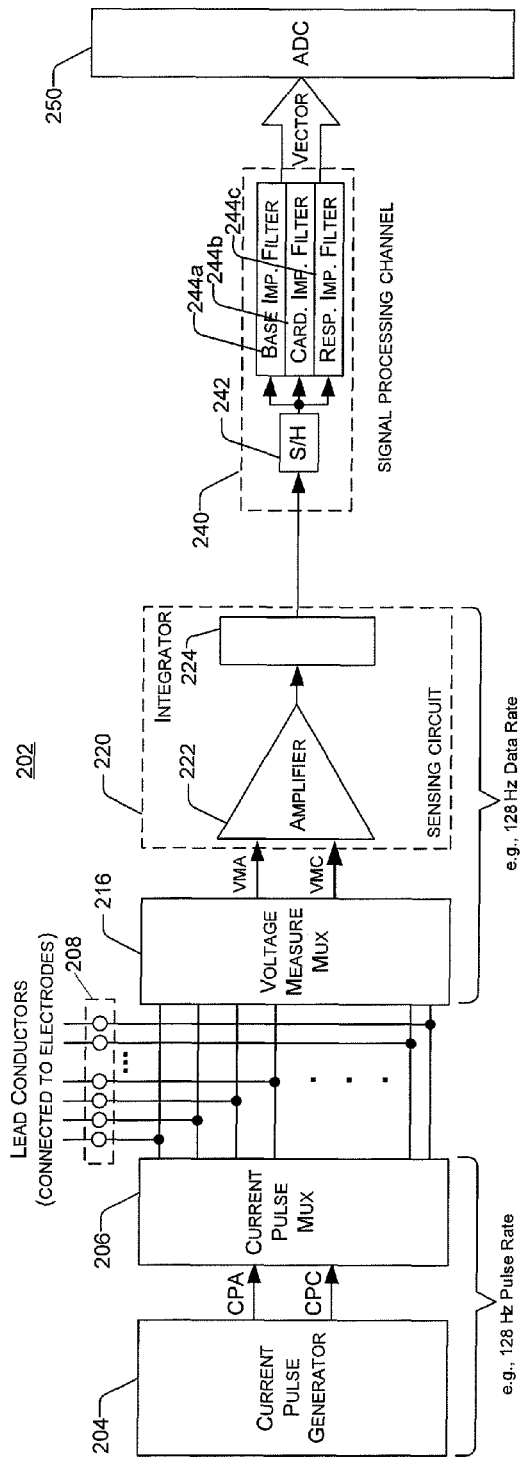
FIG. 2A is a block diagram of exemplary prior art impedance measurement and processing circuitry.
Figure 2B:
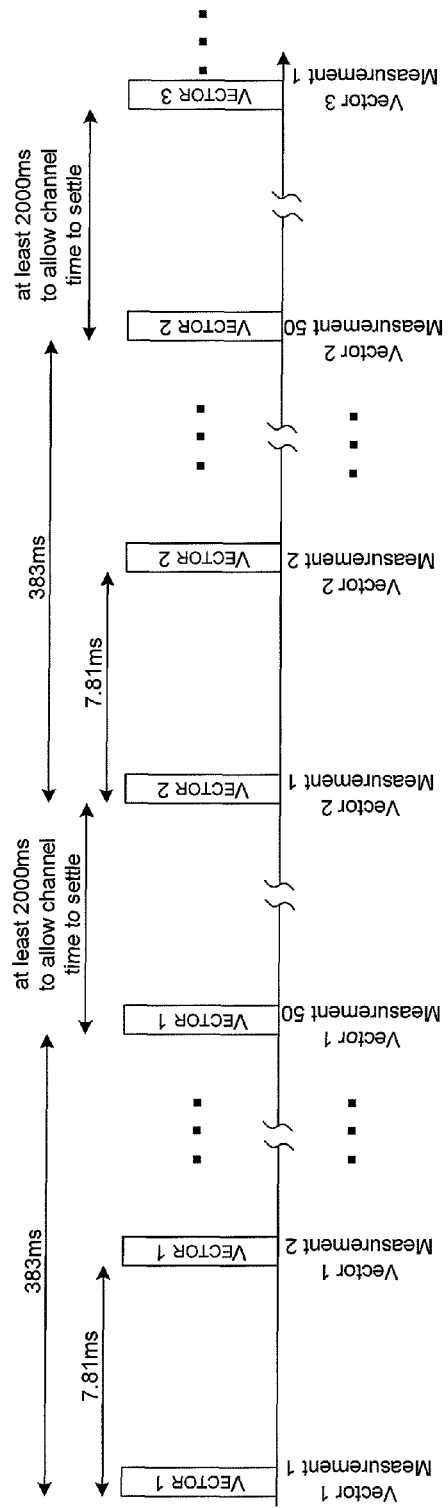
FIG. 2B is a timing diagram that is used to explain the operation and limitations associated with the prior art impedance measurement and processing circuitry shown in FIG. 2A.

In the discussion of FIGS. 2A and 2B above, there was an explanation of why the impedance measurement hardware 202 in FIG. 2A would require at least 6.56 seconds to obtain 50 impedance measurement for each of the four (4) separate vectors, where the pulse rate and sampling rate associated with each separate vector is 128 Hz. By contrast, by using the impedance measurement and processing circuitry 302 described with reference to FIG. 3B, only 389 ms is required to obtain 50 impedance measurement for each of the four (4) of the different vectors, where the pulse rate and sampling rate associated with each separate vector is still 128 Hz. The 389 ms required by the circuitry 302 is approximately 17 times faster than the 6.56 seconds required by the circuitry 202, and thus, at least an order of magnitude faster. This provides numerous advantages, as will be described below. Even if the pulse rate and sampling rate used with the impedance measurement hardware 202 in FIG. 2A was quadrupled from 128 Hz to 512 Hz, it would still take at least 6.10 seconds to obtain 50 impedance measurement for each of the four (4) different vectors, i.e., (96 ms×4)+(1.95 ms×3)+(3×2 seconds)=6.10 seconds. This is because it would still be necessary to wait at least 2 seconds (or some other relatively long period of time) after switching from one vector to another before beginning to obtain impedance measurements for the later vector, in order to give the filters 244 sufficient settle time between vectors.

As can be appreciated from the above discussion, by using the impedance measurement and processing circuitry 302, the time required to obtain cardiogenic impedance or other dynamic impedance (such as respiratory impedance) measurements can be shortened significantly. Additionally, even when obtaining impedance measurements for the purpose of checking lead, electrode and/or device integrity, e.g., when measuring a pacing lead impedance (PLI) and/or a high voltage lead integrity check (HVLIC), such impedance measurements can all be completed almost instantaneously.

Additionally, by using the impedance measurement and processing circuitry 302, more robust features can be achieved by combining the measurements obtained from multiple impedance vectors. For example, a weighted spatial average of multiple impedance vectors can be used as a combo vector which has an overall best signal variation, increased signal-to-noise ratio, consistency across subjects, etc. The spatial averaging is more advantageous compared to sequential averaging in that beat-by-beat impedance signals can be obtained and recorded (i.e., stored). This allows for detection of time-varied impedance indicative of underlying physiological changes, which would otherwise be lost in sequentially averaged impedance data that could be obtained using the impedance measurement and processing circuitry 202 of FIG. 2A. In other words, embodiments of the present invention enable a plurality of separate impedance signals to be obtained at substantially the same time so that beat to beat impedance information is available for real time evaluation of cardiac function, respiratory function, arrhythmia discrimination, etc. Additionally, because the plurality of separate impedance signals are obtained at substantially the same time, they can be readily combined (e.g., using averaging and/or subtraction) to thereby provide one or more combined impedance signals that are available for real time evaluation of cardiac function, respiratory function, arrhythmia discrimination, etc.

In specific embodiments, different vectors that cover different parts of the heart and lungs can also be combined in various different ways to satisfy various different ultimate goals (e.g. heart failure exacerbation detection).

In other embodiments, the impedance measurement and processing circuitry 302 can be used to distinguish one physiologic parameter from another. For example, instead of (or in addition to) combining several vectors together, these embodiments subtract information from a far-field or global vector using substantially simultaneous information from multiple channels to derive more local information specific to a specific component or region of interest. For a specific example, impedance measurements obtained using an RV coil electrode to SVC coil electrode vector usually include volumetric changes in both the atria and ventricles. By substantially simultaneously obtaining impedance measurements from another vector, which is sensitive to atrial contractions, the two impedance signals can be mathematically weighed and subtracted yielding an output that is primarily specific to the ventricular volumetric changes. Since each of the multiple channels is programmable in sampling rate, gain, and frequency response, the impedance signal enhancement can be accomplished with multiple impedance measurements from various organs or parts of the body. An additional discussion of such embodiments is included below in the discussion of FIG. 6.

Multi-channel impedance measurement design can also provide an alternative method to improve the far-field impedance measurement, which is currently achieved by using 3-node or 4-node measurements. One of the challenges in detecting impedance variation that reflects physiological parameters such as cardiac volume or respiratory volume is the confounding factor of the near-field impedance. The near-field impedance reflects impedance local to the electrode-tissue interface. However, due to the high current density in the near field, its contribution to the overall impedance measurement is overwhelming and can often mask the smaller contribution of the far-field impedance. With specific embodiments of the present invention, the far field impedance signal can be significantly enhanced by subtracting the near-field impedance signal from the total impedance value. For example, channel 1 can be programmed to obtain voltage measurements indicative of impedance between an LV tip electrode (e.g., 414 in FIG. 4) and a Case electrode (e.g., 500 in FIG. 5) (Vector 1), and channel 2 can be configured to obtain voltage measurements indicative of impedance between the LV tip electrode (e.g., 414 in FIG. 4) and an LV ring electrode (e.g., 416 in FIG. 4) (Vector 2). Vector 1 measures far-field plus near-field (at the tip) impedance while Vector 2 reflects mostly the near-field impedance from both the tip and the ring electrodes. By subtracting a percentage (e.g., 50%) of the Vector 2 impedance from the Vector 1 impedance, an approximation of the far-field impedance can be reconstructed substantially free of the near-field interference. An impedance processing module (e.g., 540 in FIG. 5) can implement such functionality using hardware, firmware, or software or combinations thereof. An additional discussion of such embodiments is included below in the discussion of FIG. 6.

The electrodes used to deliver current pulses (output by the current pulse generator 304) can be the same as the electrodes used to measure the voltage response to the delivered current pulses. In other words, when obtaining voltage measurements indicative of impedance, the output multiplexer 306 can be connected to the same electrodes (and more specifically, to the same electrode terminals) as the input multiplexer 316. Explained another way, the multiplexers 306 and 316 can be independently controlled to cause the current pulse anode (CPA) and the voltage measurement anode (VMA) to be the same, and the current pulse cathode (CPC) and the voltage measurement cathode (VMC) to be the same. In this configuration, the impedance measurements can be referred to as bipolar measurements. Alternatively, the electrodes used to deliver current pulses (output by the current pulse generator 304) can be the completely different than the electrodes used to measure the voltage response to the delivered current pulses. In other words, the output multiplexer 306 can be connected to the completely different electrodes (and more specifically, to completely different electrode terminals) than the input multiplexer 316. Explained another way, the multiplexers 306 and 316 can be controlled to cause the CPA and the VMA to be different, and the CPC and the VMC to be different. In this configuration, the impedance measurements can be referred to as quadripolar measurements. It is also possible that the multiplexers 306 and 316 are controlled to cause the CPA and the VMA to be different, and the CPC and the VMC to be the same, in which case the impedance measurements can be referred to a tripolar measurements. Other variations are possible, and within the scope of embodiments of the present invention.

Referring to FIG. 3A, in accordance with specific embodiments, the analog signals output by the filters 344 are voltage signals indicative of impedances associated with selected sensing vectors. Each such voltage signal can be converted to an impedance signal, using well known techniques, after the analog-to-digital conversion by the ADC 350. In other words, voltage-to-impedance conversions can be performed in the digital domain. Such a conversion can be performed, e.g., at the end of a triphasic pulse train. Since the current pulses produced by the current pulse generator 304 have known amplitudes and pulse widths, the impedance can be determined by calculating the ratio of the voltage area over the current area for each pulse train. Such calculations, which may also incorporate a calibration coefficient and/or take into account amplifier gain settings, can be digitally performed by an impedance processing module (e.g., module 540 in FIG. 5).

In accordance with alternative embodiments, voltage-to-impedance conversions can be performed in the analog domain, prior to the analog-to-digital conversions by the ADC 350. For example, this can be achieved by including voltage-to-impedance conversion circuitry within each signal path, upstream of the ADC 350, e.g., between the filters 344 and the ADC 350, but not limited thereto.

The ADC 350 can be implemented as a single ADC sampling in multiple different phases of a fast clock using an internal multiplexer. Alternatively, the ADC 350 can be implemented using multiple (e.g., four) ADCs, each of which corresponds to a different one of the sensing vectors (e.g., Vector1, Vector2, Vector3 and Vector4).

As mentioned above, impedance signals corresponding to different sensing vectors can be weighted and combined, e.g., by subtracting one impedance signal from another, or by adding impedance signals. Such weightings and/or subtractions (or additions) can be performed before or after the signals are converted from voltage signals to impedance signals. It is also noted that such weightings and/or subtractions (or additions) can be performed before or after the signals are converted from analog signals to digital signals.

Figure 3C:
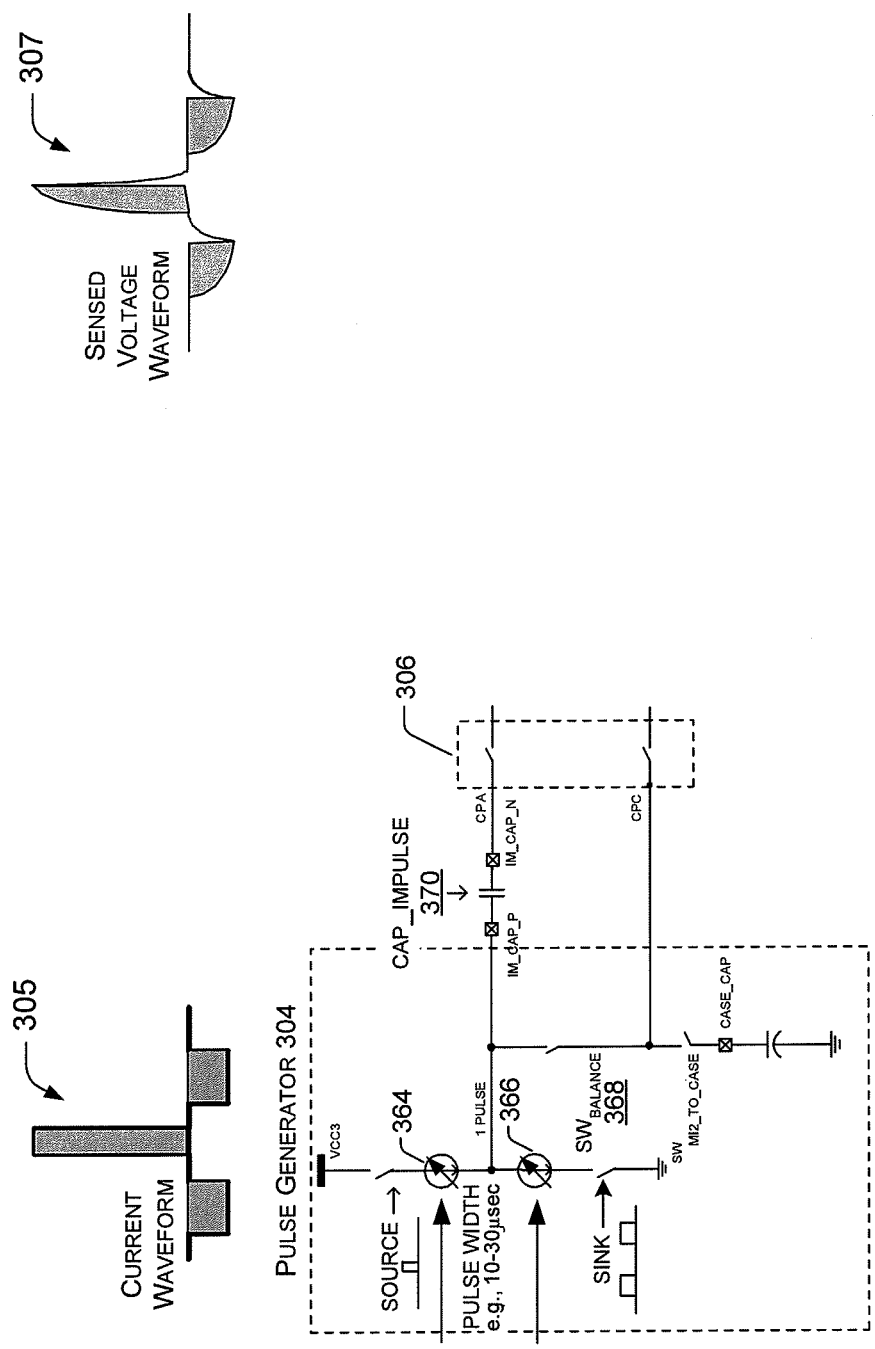
FIG. 3C illustrates exemplary details of the current pulse generator of FIG. 3A, and an exemplary multiphasic current pulse waveform generated by the current pulse generator and corresponding sensed voltage waveform.

Exemplary details of the current pulse generator 304, introduced in the discussion of FIG. 3A, will now be described with reference to FIG. 3C. Referring to FIG. 3C, the current pulse generator 304 is shown as including two timing-controlled current generators 364 and 366 with programmable magnitude. The first current generator 364 sources current, the other current generator 366 sinks the current. As part of the charge and voltage balancing process, a switch $SW_{Balance}$ 368 is used to discharge an external capacitor Cap_Impulse 370 after each generated impulse. The pulse rate is programmable. Also shown in FIG. 3C is an exemplary triphasic pulse 305, generated by the current pulse generator 304 for application to the bodily tissue of a patient, and a corresponding sensed voltage waveform 307 that is sensed by the sensing circuit 320 in FIG. 3A.

The pulse waveform 305 possesses many special waveform features and electrical characteristics that are well suited for probing and measuring many types of physiological parameters in the body using current modulated or voltage modulated pulses. Additional details of such waveforms are described, as introduced above, in U.S. Pat. No. 8,010,196 to Wong et al, entitled "Tissue Characterization Using Intracardiac Impedances with an Implantable Lead System," issued Aug. 30, 2011, and incorporated herein by reference in its entirety. Exemplary waveform 305 is multi-phasic, with a negative phase (the pulse segment below baseline) that balance a positive phase (the pulse segment above baseline). The illustrated waveform 305 is tri-phasic. Other versions of the waveform 305 may have more than three phases, may be synchronous or asynchronous, may be rectangular or sinusoidal, etc. One version of the waveform 305 uses the sinc(x) sampling waveform. In one variation, the exemplary impedance measurement architecture applies the waveform 305 as a voltage waveform instead of a current waveform and senses the results as electrical current instead of voltage.

Properties of the exemplary waveforms 305 include superior penetration of some tissues than conventionally injected signals; better differential penetration of tissues than conventionally injected signals for improved differentiation and characterization of tissues; broader frequency spectrum content than conventionally injected signals in order to characterize tissue; greater neutrality in the body than conventionally injected signals, i.e., the exemplary waveforms do not change the parameter they are trying to measure, and moreover, do not create ionic imbalances or imbalances of charge, voltage, etc., in the tissues or at tissue-electrode interfaces.

The exemplary waveform 305 provides an elegant and reliable vehicle for measuring bodily impedances in a manner that gives reliably reproducible results. Instead of a conventional technique of trying to sense an instantaneous "snapshot" measurement of a conventionally injected signal, the impedance measurement circuit architecture 302 derives an impedance measurement by dividing the area under the sensed voltage curve (waveform 307) by the area of the injected current waveform 305. An exemplary implantable device 400 (discussed below) can perform this exemplary method by "integrating the curve" of an absolute value of waveforms 305 or 307. Sometimes the exemplary implantable device can closely approximate this integration without having to perform an integration operation by directly measuring and summing the area "under" the curve (e.g., under the rectangular wave) of the waveform 305, that is, the area composed of the absolute value of the three areas of the three phases of an exemplary tri-phasic waveform 305.

Likewise, the exemplary implantable device can integrate, or closely approximate the integration, by measuring and summing the area "under" the curve (e.g., the rectangular wave) of the waveform 307, that is, the area composed of the absolute value of the three areas of the three phases. In one implementation, the area of the sensed voltage, waveform 307, is measured at the output of an integrator circuit. The area of the injected current, waveform 305, is computed by, or preset by, the micro-controller driving the implantable device. An implantable device 400, discussed below with reference to FIGS. 4 and 5, may thus use this area-based ("areal") approach to deriving a network of impedance measurements over a multi-vector network 450. Additional details of the exemplary waveforms 305 and 307, and their benefits, can be appreciated from the '196 patent that was incorporated herein by reference above.

In the above description, the pulse generator 304 was described as being a current pulse generator that produces current pulses, and the sensing circuit 320 was described as being used to sense voltage signals indicative of impedances associated with selected sensing vectors. In alternative embodiments, a voltage pulse generator that produces voltage pulses can be used in place of the current pulse generator, in which case the sensing circuit would be configured to sense current signals indicative of impedance. The sensed current signals can then be converted to impedance signals using well known techniques, either before or after analog-to-digital conversions. While such alternative embodiments are also within the scope of the present invention, for consistency, the remainder of this description will typically focus on the electrical pulses being current pulses, and on the sensed signals being voltage signals.

Exemplary Implantable Medical Device

The impedance measurement and processing circuitry 302, described above with reference to FIGS. 3A and 3B, can be incorporated into an implantable medical device, to which are connected leads, with each lead including one or more electrodes. Accordingly, before describing further embodiments of the present invention and providing additional details of embodiments of the present invention, an exemplary lead system and an exemplary implantable device are now described to provide an example environment for hosting the subject matter of embodiments of the present invention.

Figure 4:
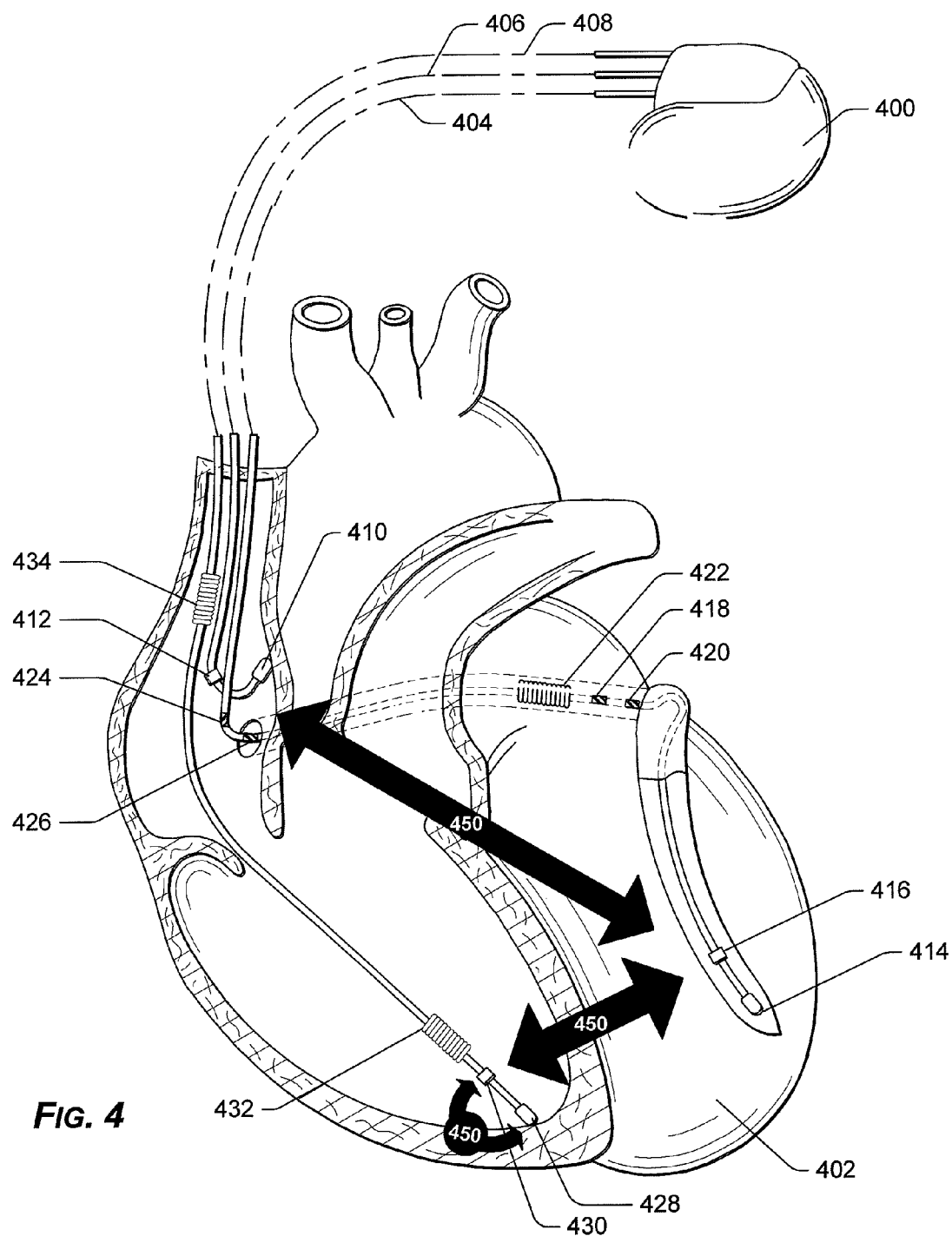
FIG. 4 illustrates an exemplary implantable medical device in electrical communication with a patient's heart, wherein the implantable medical device can include the impedance measurement and processing circuitry shown in FIG. 3A.

As shown in FIG. 4, an exemplary implantable medical device ("implantable device" 400), in this case an exemplary implantable cardioverter-defibrillator (ICD), is in electrical communication with a patient's heart 402 by way of three leads, 404, 406 and 408, suitable for sensing, delivering multi-chamber stimulation and shock therapy. Not every configuration has all of the illustrated electrodes, but a given actual configuration may include some of the illustrated electrodes and/or even more electrodes than illustrated.

To sense atrial cardiac signals and to provide right atrial chamber stimulation therapy, the implantable device 400 is coupled to an implantable right atrial lead 406, typically having an atrial tip electrode 410 and an atrial ring electrode 412, which typically is implanted in the patient's right atrial appendage. Implantable device 400 is also known as and referred to as a pacing device, a pacing apparatus, a cardiac rhythm management device, or an implantable cardiac stimulation device. Alternatively, the implantable device 400 could be a defibrillator, or cardioverter, or have combined pacing and defibrillation/cardioversion capabilities.

To sense left atrial and ventricular cardiac signals and to provide left chamber pacing therapy, the implantable device 400 is coupled to a "coronary sinus" lead 404 designed for placement in the "coronary sinus region" via the coronary sinus opening for positioning a distal electrode adjacent to the left ventricle or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

Accordingly, an exemplary coronary sinus lead 404 is designed to receive atrial and ventricular cardiac signals and to deliver left ventricular pacing therapy using a LV tip electrode 414 and a LV ring electrode 416. Left atrial pacing therapy uses, for example, first and second left atrial (LA) ring electrodes 418 and 420. Shocking therapy can be performed using at least a left atrial (LA) coil electrode 422. For a description of an exemplary coronary sinus lead, see U.S. Pat. No. 7,313,444 (Pianca et al.) entitled "A Self-Anchoring Coronary Sinus Lead" and U.S. Pat. No. 5,466,254 (Helland) entitled "Coronary Sinus Lead with Atrial Sensing Capability," which patent documents are incorporated herein by reference. Coronary sinus lead 404 may also include a pair of right atrial (RA) ring electrodes 424 and 426, which may be used to provide right atrial chamber pacing therapy.

The implantable device 400 is also shown in electrical communication with the patient's heart 402 by way of an implantable right ventricular lead 408, typically having an right ventricular (RV) tip electrode 428, an RV ring electrode 430, an RV coil electrode 432, and a superior vena cava (SVC) coil electrode 434 (also known as a right atrial (RA) coil electrode). Typically, the right ventricular lead 408 is transvenously inserted into the heart 402 so as to place the right ventricular tip electrode 428 in the right ventricular apex so that the RV coil electrode 432 will be positioned in the right ventricle and the SVC coil electrode 434 will be positioned in the superior vena cava. Accordingly, the right ventricular lead 408 is capable of receiving cardiac signals, and delivering stimulation in the form of pacing and shock therapy to the right ventricle.

A multi-vector network 450 can obtain impedance measurements over multiple vectors simultaneously, quasi-simultaneously, or sequentially using any of the electrodes illustrated in FIG. 4, either in pairs or in combinations of three or more electrodes. For the sake of illustration, an exemplary multi-vector network 450 is shown in FIG. 4. Although the illustrated multi-vector network 450 includes three vectors, other exemplary multi-vector networks 450 may include more (or less) than three vectors. The illustrated multi-vector network 450 includes three intracardiac vectors: a vector between the LV chamber and the RA chamber, a vector between the LV chamber and the RV chamber, and a vector between two electrodes in the RV chamber.

The term "multi-vector network 450" will be used herein to refer to any multi-vector network with two or more vectors between physical, logical, and or virtual electrodes, such as between the physical electrodes illustrated in FIG. 4. In the description below, "multi-vector network 450" sometimes includes at least one intracardiac vector—a vector confined to within cardiac tissue, or within the pericardial sac.

Figure 5:
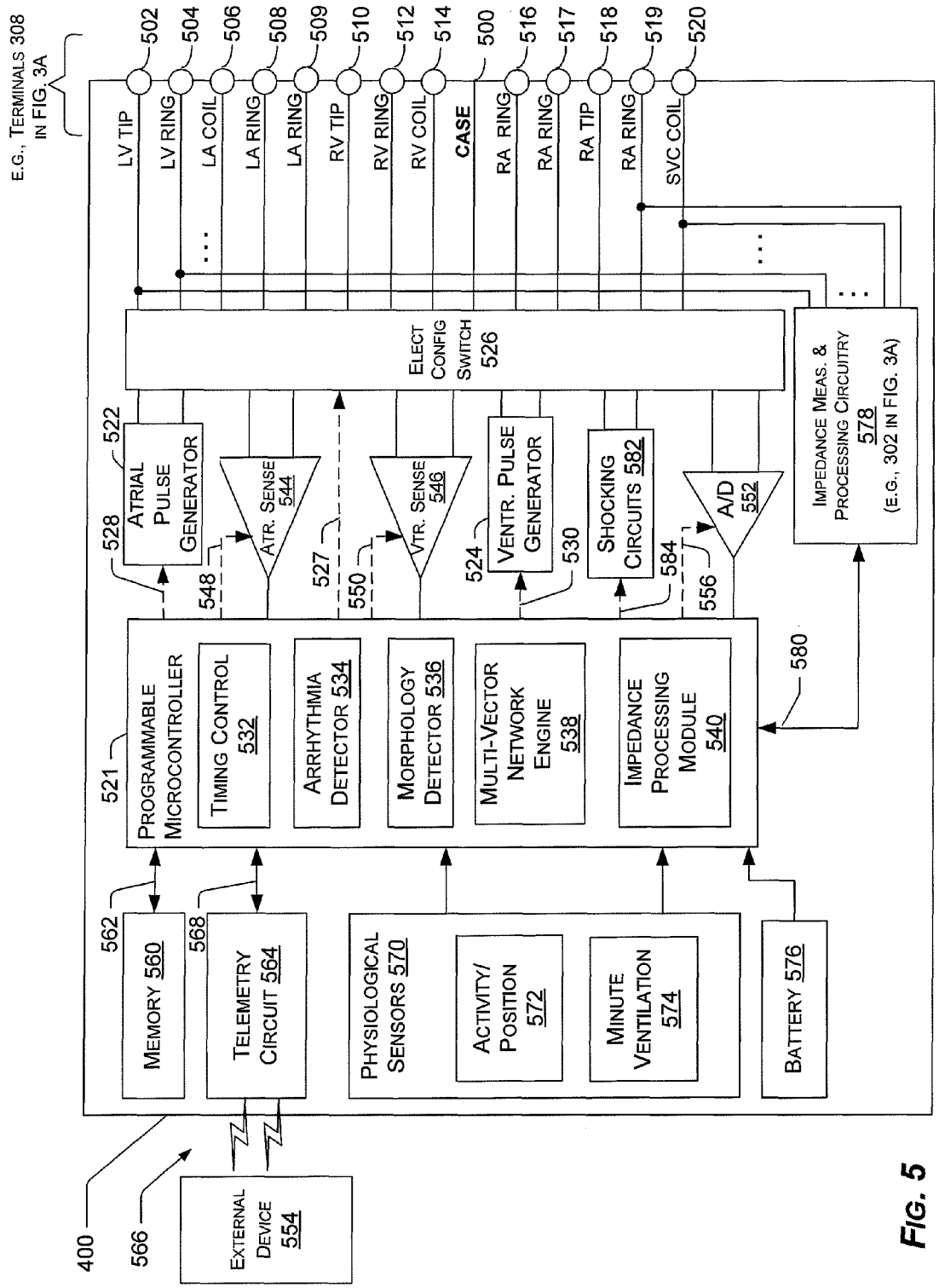
FIG. 5 is a block diagram depicting various components of the exemplary implantable medical device of FIG. 4, according to an embodiment of the present invention.

FIG. 5 shows an exemplary block diagram depicting various components of the exemplary implantable device 400. The components are typically contained in a case 500, which is often referred to as the "can", "housing", "encasing", or "case electrode", and may be programmably selected to act as the return electrode for unipolar operational modes. The case 500 may further be used as a return electrode alone or in combination with one or more of the coil electrodes 422, 432, 434 for stimulating purposes. The case 500 further includes a connector (not shown) having a plurality of terminals (502, 504, 506, 508, 509, 510, 512, 514, 516, 517, 518, 519, and 520—shown schematically with the names of the electrodes to which they are connected shown next to the terminals), including:

- a left ventricular tip terminal (LV TIP) 502 for left ventricular tip electrode 414;
- a left ventricular ring terminal (LV RING) 504 for left ventricular ring electrode 416;
- a left atrial shocking terminal (LA COIL) 506 for left atrial coil electrode 422;
- a left atrial ring terminal (LA RING) 508 for left atrial ring electrode 418;
- a left atrial ring terminal (LA RING) 509 for left atrial ring electrode 420;
- a right ventricular tip terminal (RV TIP) 510 for right ventricular tip electrode 428;
- a right ventricular ring terminal (RV RING) 512 for right ventricular ring electrode 430;
- a right ventricular shocking terminal (RV COIL) 514 for RV coil electrode 432;
- a right atrial ring terminal (RA RING) 516 for atrial ring electrode 424;
- a right atrial ring terminal (RA RING) 517 for right atrial ring electrode 426;
- a right atrial tip terminal (RA TIP) 518 for atrial tip electrode 410;
- a right atrial ring terminal (RA RING) 519 for atrial ring electrode 412; and
- a SVC shocking terminal (SVC COIL) 520 for right atrial SVC coil electrode 434.

The terminals 502, 504, 506, 508, 509, 510, 512, 514, 516, 517, 518, 519 and 520 are examples of the terminals 308 that are connected to the output multiplexer 306 and the input multiplexer 316 of the impedance measurement and processing circuitry 302 in FIG. 3A. The electrodes 410, 412, 414, 416, 418, 420, 422, 424, 426, 428, 430, 432, 434 and 500 are examples of the electrodes referred to in the discussion of FIGS. 3A and 3B.

The exemplary implantable device 400 may include a programmable microcontroller 521 that controls various operations of the implantable device 400, including cardiovascular monitoring, hemodynamic monitoring, and cardiovascular stimulation therapy. The microcontroller 521 can include a microprocessor (or equivalent control circuitry), RAM and/or ROM memory, logic and timing circuitry, state machine circuitry, and/or I/O circuitry, but is not limited thereto.

The exemplary implantable device 400 may further include an atrial pulse generator 522 and a ventricular pulse generator 524 that generate pacing stimulation pulses for delivery by the right atrial lead 406, the coronary sinus lead 404, and/or the right ventricular lead 408 via an electrode configuration switch 526. The electrode configuration switch 526 may include multiple switches for connecting the desired electrodes to the appropriate I/O circuits, thereby providing complete electrode programmability. Accordingly, switch 526, in response to a control signal 527 from the microcontroller 521, determines the polarity of the stimulation pulses (e.g., unipolar, bipolar, etc.) by selectively closing the appropriate combination of switches.

To provide stimulation therapy in each of the four chambers of the heart, the atrial and ventricular pulse generators 522 and 524 may include dedicated, independent pulse generators, multiplexed pulse generators, or shared pulse generators. The pulse generators 522 and 524 are controlled by the microcontroller 521 via appropriate control signals 528 and 530, respectively, to trigger or inhibit the stimulation pulses.

Microcontroller 521 is illustrated as including timing control circuitry 532 to control the timing of the stimulation pulses (e.g., pacing rate, atrioventricular (AV) delay, atrial interconduction (A-A) delay, or ventricular interconduction (V-V) delay, native atrial event to native or stimulated ventricular event (PV) delay, (AV/PV) delay, etc.). The timing control circuitry may also be used for the timing of refractory periods, blanking intervals, noise detection windows, evoked response windows, alert intervals, marker channel timing, and so on.

Microcontroller 521 may also implement an arrhythmia detector 534, a morphology detector 536, a multi-vector network engine 538, and an impedance processing module 540. The microcontroller 521 may process input from physiological sensors 570, such as accelerometers of an activity/position module 572, and a minute ventilation module 574, etc., The components 534, 536, 538, and 540 may be implemented in hardware as part of the microcontroller 521, or as software/firmware instructions programmed into an implementation of the implantable device 400 and executed on the microcontroller 521 during certain modes of operation. Although not shown, the microcontroller 521 may further include other dedicated circuitry and/or firmware/software components that assist in monitoring various conditions of the patient's heart and managing pacing therapies.

Atrial sensing circuits 544 and ventricular sensing circuits 546 may also be selectively coupled to the right atrial lead 406, coronary sinus lead 404, and the right ventricular lead 408, through the switch 526 to detect the presence of cardiac activity in each of the four chambers of the heart The sensing circuits 544 and 546 may include dedicated sense amplifiers, multiplexed amplifiers, or shared amplifiers. Switch 526 determines the "sensing polarity" of the cardiac signal by selectively closing the appropriate switches. In this way, the clinician may program the sensing polarity independent of the stimulation polarity.

Each sensing circuit 544 and 546 may employ one or more low power precision amplifiers with programmable gain and/or automatic gain control, bandpass filtering, and a threshold detection circuit to selectively sense the cardiac signal of interest. The automatic gain control enables the exemplary implantable device 400 to sense low amplitude signal characteristics of atrial or ventricular fibrillation.

The outputs of the atrial and ventricular sensing circuits 544 and 546 are connected to the microcontroller 521 which, in turn, is able to trigger or inhibit the atrial and ventricular pulse generators 522 and 524 in a demand fashion in response to the absence or presence of cardiac activity in the appropriate chambers of the heart. The sensing circuits 544 and 546 receive control signals from the microcontroller 521 over signal lines 548 and 550 to control, for example, the gain and the timing of blocking circuitry (not shown) optionally coupled to the inputs of the sensing circuits 544, 546.

Cardiac signals, including signals involved in impedance measurements, are supplied to an analog-to-digital (ND) data acquisition system 552, which is configured to acquire these signals, convert the raw analog data into a digital signal, and store the digital signals for later processing and/or telemetric transmission to an external device 554. The data acquisition system 552 is coupled to the right atrial lead 406, the coronary sinus lead 404, and the right ventricular lead 408 through the switch 526 to process signals across any pair of desired electrodes.

The data acquisition system 552 is coupled to the microcontroller 521, or other detection circuitry, to assist in detecting an evoked response from the heart 402 in response to an applied stimulus, which is often referred to as detecting "capture". Capture occurs when an electrical stimulus applied to the heart is of sufficient energy to depolarize the cardiac tissue, thereby causing the heart muscle to contract. The microcontroller 521 detects a depolarization signal during a window following a stimulation pulse, the presence of which indicates that capture has occurred. The microcontroller 521 enables capture detection by triggering the ventricular pulse generator 524 to generate a stimulation pulse, starting a capture detection window using the timing control circuitry 532 within the microcontroller 521, and enabling the data acquisition system 552 via control signal 556 to sample the cardiac signal that falls in the capture detection window and, based on the amplitude, determines if capture has occurred.

The microcontroller 521 is further coupled to a memory 560 by a suitable data/address bus 562. The programmable operating parameters used by the microcontroller 521 are stored in memory 560 and used to customize the operation of the exemplary implantable device 400 to suit the needs of a particular patient. Such operating parameters define, for example, pacing pulse amplitude, pulse duration, electrode polarity, rate, sensitivity, automatic features, arrhythmia detection criteria, and the amplitude, wave shape and vector of each shocking pulse to be delivered to the patient's heart 402 within each respective tier of therapy.

The operating parameters of the exemplary implantable device 400 may be non-invasively programmed into the memory 560 through a telemetry circuit 564 in telemetric communication via communication link 566 with the external device 554, such as a programmer, local transceiver, or a diagnostic system analyzer. The microcontroller 521 can activate the telemetry circuit 564 with a control signal 568. The telemetry circuit 564 allows intracardiac electrograms and status information relating to the operation of the exemplary implantable device 400 (as contained in the microcontroller 521 or memory 560) to be sent to the external device 554 through an established communication link 566.

The physiological sensors 570 referred to above can further include, for example, "rate-responsive" sensors that adjust pacing stimulation rates according to the exercise state of the patient. Accordingly, the microcontroller 521 responds by adjusting the various pacing parameters (such as rate, etc.) at which the atrial and ventricular pulse generators 522 and 524 generate stimulation pulses.

The physiological sensors 570 may include mechanisms and sensors to detect bodily movement (572), minute ventilation 574, changes in blood pressure, changes in cardiac output, changes in the physiological condition of the heart, diurnal changes in activity (e.g., detecting sleep and wake states), G-force acceleration of the ICD case 500, length of the cardiac QT interval, blood oxygen saturation, blood pH, changes in temperature, respiration rate, and QRS wave duration. While shown as being included within the exemplary implantable device 400, the physiological sensor(s) 570 may also be external to the exemplary implantable device 400, yet still be implanted within or carried by the patient, e.g., a blood pressure probe. Examples of physiological sensors external to the case 500 that may be deployed by implantable device 400 include sensors that, for example, sense respiration activities, $O_2$ saturation, evoked response, pH of blood, and so forth.

The illustrated physiological sensors 570 include one or more activity/position sensors 572 (e.g., 1D or 3D accelerometers, movement sensors, etc.) to detect changes in the patient's position. The activity/position sensors 572 can be used to assist detection of orthostatic hypotension caused by transition from a less upright posture to a comparatively more upright posture. One example postural change leading to orthostatic hypotension in susceptible individuals is a movement from a supine position in a rest state (e.g., sleeping in bed) to an upright position in a non-rest state (e.g., sitting or standing up).

In one configuration, accelerometer output signal is band-pass-filtered, rectified, and integrated at regular timed intervals. A processed accelerometer signal can be used as a raw activity signal. The device derives an activity measurement based on the raw activity signal at intervals timed according to the cardiac cycle. The activity signal alone can be used to indicate whether a patient is active or resting. The activity measurement can further be used to determine an activity variance parameter. A large activity variance signal is indicative of a prolonged exercise state. Low activity and activity variance signals are indicative of a prolonged resting or inactivity state.

The minute ventilation (MV) sensor 574 may also be included in the physiological sensors 570 in order to sense rate and depth of breathing. Minute ventilation can be measured as the total volume of air that moves in and out of a patient's lungs in a minute. The MV sensor 574 may use impedance measurement and processing circuitry 578 to sense air movement by measuring impedance across the chest cavity.

The impedance measurement and processing circuitry 578 can be implemented using the circuitry 302 described above with reference to FIGS. 3A and 3B. This circuitry 302 can communicate with the microcontroller 521, e.g., via control signals 580 and can be used for obtaining many types of bodily and intracardiac impedances, including a network of single- or multi-vector impedance measurements. Such impedance measurements can be used for trending many kinds of physiological variables, and can also be used for detection of air movement in and out of the lungs, blockage of airways, lead impedance surveillance during acute and chronic phases for proper lead positioning or dislodgement; lead integrity by detecting insulation abrasion, operable electrodes, and automatically switching to an operable pair if dislodgement occurs; measuring respiration or minute ventilation; measuring thoracic impedance for determining shock thresholds; detecting when the device has been implanted; measuring cardiac stroke volume; detecting the opening of heart valves; and so forth. The impedance measurement and processing circuitry 578 is shown as being connected to each of the terminals 502, 504, 506, 508, 509, 510, 512, 514, 516, 517, 518, 519 and 520. Through use of switching circuitry (e.g., input and output multiplexers 306 and 316 in FIG. 3A) the impedance measurement and processing circuitry 578 can be connected to any desired electrode combinations, and networks of vectors can be selected by the multi-vector network engine 538.

The exemplary implantable device 400 additionally includes a battery 576 that provides operating power to all of the components shown in FIG. 5. The battery 576 is capable of operating at low current drains for long periods of time (e.g., less than 10 µA), and is capable of providing high-current pulses (for capacitor charging) when the patient requires a shock pulse (e.g., in excess of 10 A, at voltages above 500 V, for periods of 2-20 microseconds). The battery 576 also desirably has predictable discharge characteristics so that elective replacement time can be detected. As one example, the exemplary implantable device 400 employs lithium/silver vanadium oxide batteries.

The exemplary implantable device 400 can further include magnet detection circuitry (not shown), coupled to the microcontroller 521, to detect when a magnet is placed over the exemplary implantable device 400. A magnet may be used by a clinician to perform various test functions of the exemplary implantable device 400 and/or to signal the microcontroller 521 that an external programmer (e.g., 554) is in place to receive or transmit data to the microcontroller 521 through the telemetry circuits 564.

The microcontroller 521 further controls a shocking circuit 582 via a control signal 584. The shocking circuit 582 generates shocking pulses of low (e.g., up to 0.5 joules), moderate (e.g., 0.5-10 joules), or high energy (e.g., 11-40 joules), as selected by the microcontroller 521. Such shocking pulses are applied to the patient's heart 402 through at least two shocking electrodes selected, for example, from the left atrial coil electrode 422, the RV coil electrode 432, and/or the SVC coil electrode 434. As noted above, the case 500 may act as an active electrode in combination with the RV coil electrode 432, or as part of a split electrical vector using the SVC coil electrode 434 or the left atrial coil electrode 422 (i.e., using the RV coil electrode 432 as a common electrode).

Cardioversion shocks are generally considered to be of low to moderate energy level (so as to minimize pain felt by the patient), and/or synchronized with an R-wave and pertain to the treatment of tachycardia. Defibrillation shocks are generally of moderate to high energy level (i.e., corresponding to thresholds in the range of, e.g., 5-40 joules), delivered asynchronously (since R-waves may be too disorganized), and pertain exclusively to the treatment of fibrillation. Accordingly, the microcontroller 521 is capable of controlling the synchronous or asynchronous delivery of the shocking pulses.

More generally, the exemplary implantable device 400 can be programmed to stimulate different sets of vascular and cardiac muscles through the same lead/electrode system. The exemplary implantable device 400 can be programmed to vary the output voltage of various pulses to effectively stimulate different muscles of the heart and blood vessels, even though the physical placement of leads and electrodes does not change.

Embodiments of the present invention can be used to significantly reduce the amount of time necessary to obtain dynamic impedance signals associated with multiple vectors. Exemplary dynamic impedance signal, which were discussed above, include low frequency impedance $Z_o$ (sometimes also referred to as raw impedance, or low frequency raw impedance), respiratory impedance $Z_r$, and cardiogenic impedance $Z_c$ (sometime also referred to as cardiac impedance). However, embodiments of the present invention can also be used to obtain other types of dynamic impedance measurements, as well as non-dynamic impedance measurements, such as lead impedance measurements.

Individual impedance signals obtained using embodiments of the present invention, or combinations of multiple impedance signal obtained using embodiments of the present invention (e.g., combined through addition or subtraction), can be used in various different manner for various different purposes, examples of which are discussed below. For example, cardiogenic impedance signals obtained using embodiments of the present invention can be used for monitoring hemodynamic stability, performing arrhythmia discrimination, prediction and monitoring of heart failure progression, and functioning as a hemodynamic (such as stroke volume) surrogate. For a more specific example, impedance signals that are indicative of impedance to electrical flow spanning a field extending through the lungs can be used, e.g., to assess pulmonary fluid congestion to detect pulmonary edema or heart failure, or more generally, to monitor fluid accumulation in a patient's thoracic cavity. For another example, the morphology of one or more obtained cardiogenic impedance signals can be compared to the morphology of one or more stored templates to analyze a patient's cardiac condition and/or to adjust treatment therapy. Cardiogenic impedance signals can also be used, together with an impedance plethysmography or photoplethysmography signal, to estimate arterial blood pressure. Respiratory impedance signal can be used, e.g., to track respiration rate and depth, sleep apnea, and heart failure conditions. These are just a few examples of the various uses of impedance signals, which is not meant to be limiting or all encompassing.

Figure 6:
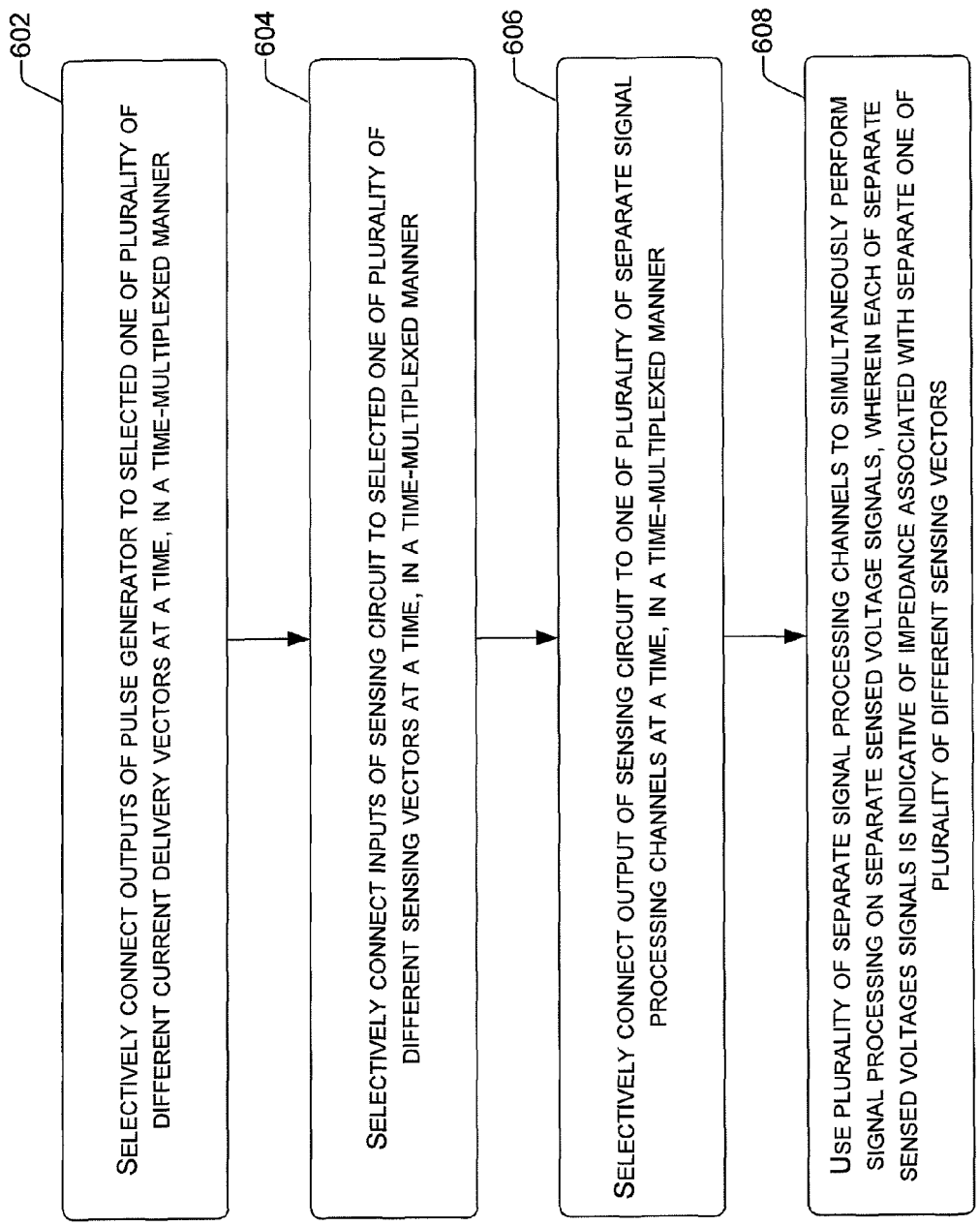
FIG. 6 is a high level flow diagram that is used to summarize methods according to various embodiments of the present invention.

The flow diagram of FIG. 6 will now be used to summarize methods of embodiments of the present invention, which have already been discussed above with reference to FIGS. 3A-3C, 4 and 5. More specifically, FIG. 6 is used to describe methods for use with an implantable system that includes a plurality of terminals configured to be connected to a plurality of implantable electrodes via electrical conductors of one or more implantable leads, a pulse generator, a sensing circuit and three multiplexers upstream of a plurality of separate signal processing channels. An example of such a system, or portion thereof, was described above with reference to FIG. 3A. A plurality of different subsets of the implantable electrodes can be used to define a plurality of different electrical pulse delivery vectors. Additionally, a plurality of different subsets of the implantable electrodes can be used to define a plurality of different sensing vectors. The pulse generator (e.g., 304) is configured to produce electrical current pulses for delivery via a selected one of the plurality of different electrical pulse delivery vectors at a time. The sensing circuit (e.g., 320) is configured to sense a voltage signal indicative of an impedance associated with a selected one of the plurality of different sensing vectors at a time. As mentioned above, a voltage pulse generator and a current sensing circuit can alternatively be used.

Referring to FIG. 6, at step 602, outputs of the pulse generator are selectively connected to a selected one of the plurality of different electrical pulse delivery vectors at a time, in a time-multiplexed manner (e.g., using the output multiplexer 306). At step 604, inputs of the sensing circuit are selectively connected to a selected one of the plurality of different sensing vectors at a time, in a time-multiplexed manner (e.g., using the input multiplexer 336). At step 606, an output of the sensing circuit (e.g., 320) is selectively connected to one of a plurality of separate signal processing channels (e.g., 340_1, 340_2, 340_3 and 340_4) at a time, in a time-multiplexed manner (e.g., using the channel multiplexer 336). At step 608, the plurality of separate signal processing channels are used to simultaneously perform signal processing on separate sensed voltage signals, wherein each of the separate sensed voltages signals is indicative of an impedance associated with a separate one of the plurality of different sensing vectors.

As was mentioned above, in accordance with certain embodiments, a first impedance signal (obtained using one or more sensing vector(s)) spans both a first region and a second region within a patient's thoracic cavity, whereas a second impedance signal (obtained using one or more further sensing vector(s)) only spans the first region (but not the second region). In this manner, a third impedance signal primarily corresponding to the second region can be obtained by subtracting the second impedance signal from the first impedance signal. As also described above, prior to such subtraction, appropriate weighting of the first and/or second impedance signals can be performed. For example, the first region can include at least one atrial chamber and at least one ventricular chamber, and the second region include the at least one atrial chamber (but not the at least one ventricular chamber). This way, the third impedance signal would, obtained through the subtraction, would be primarily indicative of the at least one ventricular chamber. For another example, the first impedance signal can be indicative of both far-field impedance and near-field impedance, and the second impedance signal can be primarily indicative of the near-field impedance but not the far-field impedance. Here, third impedance signal, obtained by subtracting the second impedance signal from the first impedance signal, can be primarily indicative of the far-field impedance. Other variations are also possible and within the scope of embodiments of the present invention.

Embodiments of the present invention have been described above with the aid of functional building blocks illustrating the performance of specified functions and relationships thereof. The boundaries of these functional building blocks have often been arbitrarily defined herein for the convenience of the description. Alternate boundaries can be defined so long as the specified functions and relationships thereof are appropriately performed. Any such alternate boundaries are thus within the scope and spirit of the claimed invention. For example, it would be possible to combine or separate some of the steps shown in FIG. 6. For another example, it is possible to change the boundaries of some of the blocks shown in FIGS. 3A and 5.

The previous description of the preferred embodiments is provided to enable any person skilled in the art to make or use the embodiments of the present invention. While the invention has been particularly shown and described with reference to preferred embodiments thereof, it will be understood by those skilled in the art that various changes in form and details may be made therein without departing from the spirit and scope of the invention.

What is claimed is:

1. An implantable system, comprising:
   a plurality of terminals configured to be connected to a plurality of implantable electrodes via electrical conductors of one or more implantable leads,
      wherein a plurality of different subsets of the implantable electrodes are used to define a plurality of different electrical pulse delivery vectors, and
      wherein a plurality of different subsets of the implantable electrodes are used to define a plurality of different sensing vectors;
   a pulse generator configured to produce one or more electrical pulses for delivery via a selected one of the plurality of different electrical pulse delivery vectors at a time;
   a sensing circuit configured to sense a signal indicative of an impedance associated with a selected one of the plurality of different sensing vectors at a time;
   a plurality of separate signal processing channels each configured to perform signal processing on a sensed signal indicative of an impedance obtained using the sensing circuit;
   a first multiplexer configured to selectively connect outputs of the pulse generator to a selected one of the plurality of different electrical pulse delivery vectors at a time;
   a second multiplexer configured to selectively connect inputs of the sensing circuit to a selected one of the plurality of different sensing vectors at a time; and
   a third multiplexer configured to selectively connect an output of the sensing circuit to one of the plurality of separate signal processing channels at a time,
   wherein the pulse generator, sensing circuitry, signal processing channels and the first, second and third multiplexers are used to obtain two or more impedance signals substantially simultaneously.

2. The implantable system of claim 1
   further comprising at least one of a processor or circuitry configured to combine the two or more impedance signals using weighted or non-weighted averaging to produce a combined impedance signal.

3. The implantable system of claim 1, wherein at least one of the following pulse parameters of at least one of the vectors differs from at least one of the pulse parameters of at least one other vector:
   pulse rate;
   pulse amplitude; or
   pulse width.

4. The implantable system of claim 1, wherein the sensing circuit comprises:
   a differential amplifier that includes
      a first input terminal that receives an anodal signal from the second multiplexer,
      a second input terminal that receives a cathodal signal from the second multiplexer, and
      an output terminal that outputs a voltage signal of a difference between the anodal and cathodal signals received at the first and second input terminals; and
   an integrator that integrates the signal output by the differential amplifier to thereby produce the sensed signal.

5. The implantable system of claim 1, wherein each of the plurality of separate signal processing channels comprises:
   a sample-and-hold circuit that receives a signal from the third multiplexer; and
   one or more filters downstream of the sample-and-hold circuit;
   wherein the one or more filters, of each of the separate signal processing channels, comprise one or more of the following
      a filter that outputs a filtered signal indicative of low frequency impedance;
      a filter that outputs a filtered signal indicative of cardiac impedance; and
      a filter that outputs a filtered signal indicative of respiratory impedance.

6. The implantable system of claim 1, wherein the pulse generator, sensing circuitry, signal processing channels and the first, second and third multiplexers are used to substantially simultaneously obtain
   a first impedance signal using one or more sensing vectors spanning both a first region and a second region within a patient's thoracic cavity; and
   a second impedance signal using one or more further sensing vector(s) spanning the first region but not the second region; and
   further comprising at least one of a processor or circuitry configured to subtract the second impedance signal from the first impedance signal to obtain a third impedance signal primarily corresponding to the second region.

7. The implantable system of claim 6, wherein:
   the first region comprises at least one atrial chamber and at least one ventricular chamber;
   the second region comprises the at least one atrial chamber or the at least one ventricular chamber, but not both of the at least one atrial chamber and the at least one ventricular chamber; and
   the third impedance signal, obtained using the at least one of a processor or circuitry configured to subtract the second impedance signal from the first impedance signal, is primarily indicative of the other one of the at least one atrial chamber and the at least one ventricular chamber.

8. The implantable system of claim 6, wherein:
the first impedance signal is indicative of both far-field impedance and near-field impedance;
the second impedance signal is primarily indicative of the near-field impedance but not the far-field impedance; and
the third impedance signal, obtained using the at least one of a processor or circuitry configured to subtract the second impedance signal from the first impedance signal, is primarily indicative of the far-field impedance.

9. The implantable system of claim 1, wherein:
the pulse generator is configured to produce electrical current pulses; and
the sensing circuit is configured to sense a voltage signal indicative of the impedance associated with a selected one of the plurality of different sensing vectors at a time.

10. An implantable system, comprising:
a plurality of terminals configured to be connected to a plurality of implantable electrodes via electrical conductors of one or more implantable leads,
wherein a plurality of different subsets of the implantable electrodes are used to define a plurality of different electrical pulse delivery vectors, and
wherein a plurality of different subsets of the implantable electrodes are used to define a plurality of different sensing vectors;
a pulse generator configured to produce one or more electrical pulses for delivery via a selected one of the plurality of different electrical pulse delivery vectors at a time;
a sensing circuit configured to sense a signal indicative of an impedance associated with a selected one of the plurality of different sensing vectors at a time;
a plurality of separate signal processing channels each configured to perform signal processing on a sensed signal indicative of an impedance obtained using the sensing circuit;
a first multiplexer configured to selective connect outputs of the pulse generator to a selected one of the plurality of different electrical pulse delivery vectors at a time;
a second multiplexer configured to selectively connect an output of the sensing, circuit to a selected one of the plurality of different sensing vectors, at a time; and
a third multiplexer configured to selectively connect an output of the sensing circuit to one of the plurality of separate signal processing channels at a time,
wherein the third multiplexer and the plurality of separate impedance processing channels enable impedances associated with the plurality of separate sensing vectors to be processed in a time interleaved manner so that impedances associated with the plurality of separate sensing vectors can be considered to correspond to a substantially same temporal data point.

11. An implantable system, comprising:
a plurality of terminals configured to be connected to a plurality of implantable electrodes via electrical conductors of one or more implantable leads,
wherein a plurality of different subsets of the implantable electrodes are used to define a plurality of different electrical pulse delivery vectors, and
wherein a plurality of different subsets of the implantable electrodes are used to define a plurality of different sensing vectors;
a pulse generator configured to produce one or more electrical pulses for delivery via a selected one of the plurality of different electrical pulse delivery vectors at a time;
a sensing circuit configured to sense a signal indicative of an impedance associated with a selected one of the plurality of different sensing vectors at a time;
a plurality of separate signal processing channels each configured to perform signal processing on a sensed signal indicative of an impedance obtained using the sensing circuit;
a first multiplexer configured to selectively connect outputs of the pulse generator to a selected one of the plurality of different electrical pulse delivery vectors at a time;
a second multiplexer configured to selectively connect inputs of the sensing circuit to a selected one of the plurality of different sensing vectors at a time; and
a third multiplexer configured to selectively connect an output of the sensing circuit to one of the plurality of separate signal processing channels at a time;
a controller configured to control the pulse generator, sensing circuitry, signal processing channels and the first, second and third multiplexers to obtain a plurality of impedance signals each of which is associated with a different sensing vector; and
at least one of a processor or circuitry configured to combine two or more of the plurality of impedance signals to obtain a combined impedance signal, wherein;
the controller is configured to control the pulse generator, sensing circuitry, signal processing channels and the first, second and third multiplexers to obtain;
a first impedance signal using one or more sensing vectors spanning both a first region and a second region within a patient's thoracic cavity; and
a second impedance signal using one or more further sensing vectors spanning the first region but not the second region; and
the at least one processor and circuitry is configured to obtain the combined impedance signal, which primarily corresponds to the second region, by subtracting the second impedance signal from the first impedance signal.

12. The implantable system of claim 11, wherein:
the first region comprises at least one atrial chamber and at least one ventricular chamber;
the second region comprises the at least one atrial chamber or the at least one ventricular chamber, but not both of the at least one atrial chamber and the at least one ventricular chamber; and
the combined impedance signal primarily corresponds to the other one of the at least one atrial chamber and the at least one ventricular chamber.

13. The implantable system of claim 12, wherein:
the first impedance signal is indicative of both far-field impedance and near-field impedance;
the second impedance signal is primarily indicative of the near-field impedance but not the far-field impedance; and
the combined impedance signal is primarily indicative of the far-field impedance.

14. An implantable system, comprising;
a plurality of terminals configured to be connected to a plurality of implantable electrodes via electrical conductors of one or more implantable leads,
wherein a plurality of different subsets of the implantable electrodes are used to define a plurality of different electrical pulse delivery vectors, and
wherein a plurality of different subsets of the implantable electrodes are used to define plurality of different sensing vectors;
a pulse generator configured to produce one or more electrical pulses for delivery via a selected one of the plurality of different electrical pulse delivery vectors at a time;

a sensing circuit configured to sense a signal indicative of an impedance associated with a selected one of the plurality of different sensing vectors at a time;

a plurality of separate signal processing channels each configured to perform signal processing on a sensed signal indicative of an impedance obtained using the sensing circuit;

a first multiplexer configured to selectively connect outputs of the pulse generator to a selected one of the plurality of different electrical pulse delivery vectors at a time;

a second multiplexer configured to selectively connect inputs of the sensing circuit to a selected one of the plurality of different sensing vectors at a time; and a third multiplexer configured to selectively connect an output of the sensing circuit to one of the plurality of separate signal processing channels at a time;

a controller configured to control the pulse generator, sensing circuitry, signal processing channels and the first, second and third multiplexers to obtain a plurality of impedance signals substantially simultaneously, each of which is associated with a different sensing vector; and at least one processor and circuitry configured to combine two or more of the plurality of impedance signals obtained substantially simultaneously to obtain a combined impedance signal, wherein the at least one of a processor or circuitry is configured to adjust the weighting of at least one of the plurality of impedance signals to produce the combined impedance signal.

* * * * *